United States Patent [19]
Pettit et al.

[11] Patent Number: 5,504,191
[45] Date of Patent: Apr. 2, 1996

[54] HUMAN CANCER INHIBITORY PENTAPEPTIDE METHYL ESTERS

[75] Inventors: George R. Pettit, Paradise Valley; Jayaram K. Srirangam, Tempe; Michael D. Williams, Mesa, all of Ariz.

[73] Assignee: Arizona Board of Regents acting on behalf of Arizona State University, Tempe, Ariz.

[21] Appl. No.: 283,682

[22] Filed: Aug. 1, 1994

[51] Int. Cl.[6] .............................. C07K 5/00; C07K 7/00; C07K 17/00; A61K 38/00
[52] U.S. Cl. .............................. 530/330; 514/17
[58] Field of Search .............................. 530/330; 514/17

[56] References Cited

PUBLICATIONS

Pettit et al J. Org. Chem vol. 59 p. 2935 (1994).

*Primary Examiner*—Howard E. Schain
*Assistant Examiner*—Sheela J. Huff
*Attorney, Agent, or Firm*—Richard R. Mybeck; Paula L. Bentley

[57] ABSTRACT

Herein disclosed are several pentapeptide methyl ester derivatives of dolastatin 10, using both naturally occurring and modified amino acids. The selected modified amino acids are constituents of dolastatin 10 which is a structurally distinct peptide with excellent in vitro and in vivo antineoplastic activity. The structures of these compounds are as shown below:

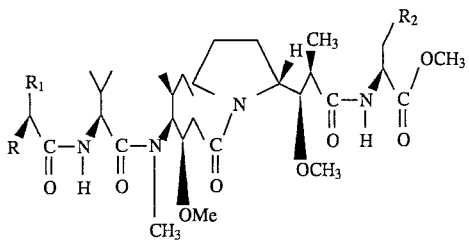

10a) $R_1 = \text{i-Pr}; R = -NH(Me)_2; R_2 = -CH_2CH_2CH_2NH\text{-cbz}$

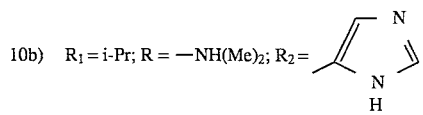

11a) $R_1 = -(CH_2)_4NH\text{-cbz}; R = -NH(\text{cbz});$

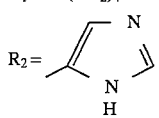

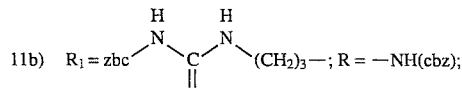

$R_2 = -CH_2CH_2CH_2NH\text{-cbz}$

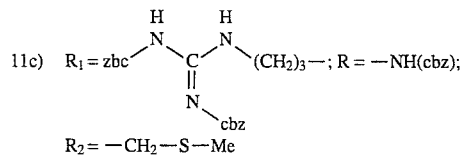

$R_2 = -CH_2-S-Me$

6 Claims, No Drawings

HUMAN CANCER INHIBITORY PENTAPEPTIDE METHYL ESTERS

Financial assistance for this project was provided by U.S. Government Grant Number OIG-CA 44344-01-04-05; and the United States Government may own certain rights to this invention.

This invention relates generally to the field of cancer chemotherapy and more particularly to the synthesis of unique pentapeptide methyl ester derivatives of dolastatin 10 which may be useful in chemotherapy.

BACKGROUND OF THE INVENTION

Ancient marine invertebrate species of the Phyla Bryozoa, Molluska, and Porifera have been well established in the oceans for over one billion years. Such organisms have undergone trillions of biosynthetic reactions of their evolutionary chemistry to reach their present level of cellular organization, regulation and defense.

Marine sponges, however, have changed minimally in their physical appearance over the last 500 million years. This suggests that they possess a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. certain sea hare extracts were being used in Greece for their curative affect. This consideration along with the observation that marine animals, e.g. invertebrates and sharks, rarely develop cancer led to the systematic investigation of marine animal and plant anticancer compounds.

By 1968, ample evidence had been obtained, based on the U.S. National Cancer Institute's (NCI) key experimental cancer study systems, that certain marine organisms could provide new and antineoplastic and/or cytotoxic agents useful in chemotherapy and might also lead to compounds which would be effective in the control and/or eradication of viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the time lag between the isolation of a new compound and its introduction to the market. Often this procedure takes several years and may take decades. As a result, industry, in association with the U.S. Government, has developed a system of testing criteria which serves two purposes. One is to eliminate those substances which are shown through testing to be economically counterproductive to pursue. The second, more important purpose serves to identify those compounds which demonstrate a high likelihood of success and therefore warrant the further study and qualification, and attendant expense, necessary to meet the stringent regulatory requirements which control the ultimate market place.

The current cost to develop the necessary data required for lawful marketing of a new drug compound approaches ten million dollars per compound. Economics dictate that such a huge investment be made only when there is a reasonable likelihood that it can be recovered. Absent such a likelihood, there will be no investment and, without investment, the research requisite for the discovery of these potentially life saving compounds will cease.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and is accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, October 1989, for an in depth description of the testing protocol; and Paull K. D., "Display and Analysis of Patterns of Differential Activity of Drugs Against Human Tumor Cell Lines; Development of Mean Graph and COMPARE Algorithm" *Journal of the National Cancer Institute Reports*, Vol. 81, No. 14, Page 1088, Jul. 14, 1989 for a description of the methods of statistical analysis employed to evaluate the test results. Both of these references are incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures possessing antineoplastic qualities. The collection and processing of these later compounds from their natural sources ranges from grossly impractical to the utterly impossible. Ignoring the ecological impact, the population of these creatures and the cost of collection and extraction make the process unworkable. Artificial synthesis of the active compounds is the only possible solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The inhibition of human cancerous tumor growth as evidenced by NCI cell line data is utilitarian in that it relieves these conditions, thereby allowing the human thus afflicted to have a longer, more productive life. Little could be more utilitarian than this result.

The sole right obtained from the grant of a Letters Patent is to prevent others from exploiting the subject matter of the patent. This results in the protection of the inventor for a period adequate to allow the recoupment of investment. This in turn provides incentive and the means for further research.

The recognition of antineoplastic and tumor inhibiting activity as demonstrated by accepted NCI criteria as "utility" can promote research efforts in the United States and is unequivocally essential if those efforts are to obtain even a modest modicum of success. To reject the NCI criteria on any grounds can only result in quashing all further efforts in the United States and leave our people at the mercy of those foreign companies who operate in more foresighted jurisdictions.

BRIEF SUMMARY OF THE INVENTION

The investigation of potentially useful antineoplastic peptides offers one of the most promising approaches to new anticancer drugs. Continuing research along these lines has now resulted in the discovery and synthesis of several new pentapeptide methyl esters. In the synthesis of these compounds, naturally occurring as well as some modified amino acids have been utilized. The modified amino acids disclosed herein are constituents of the well known dolastatin 10 which are structurally distinct peptides with excellent antineoplastic activity. Presently dolastatin 10 represents the most important member of the dolastatin family and is a potentially useful anticancer drug. Herein disclosed are new compounds having excellent activity against a series of human cancer cell lines. Structures of the compounds, with their reference numbers, and a synthesis scheme appear below:

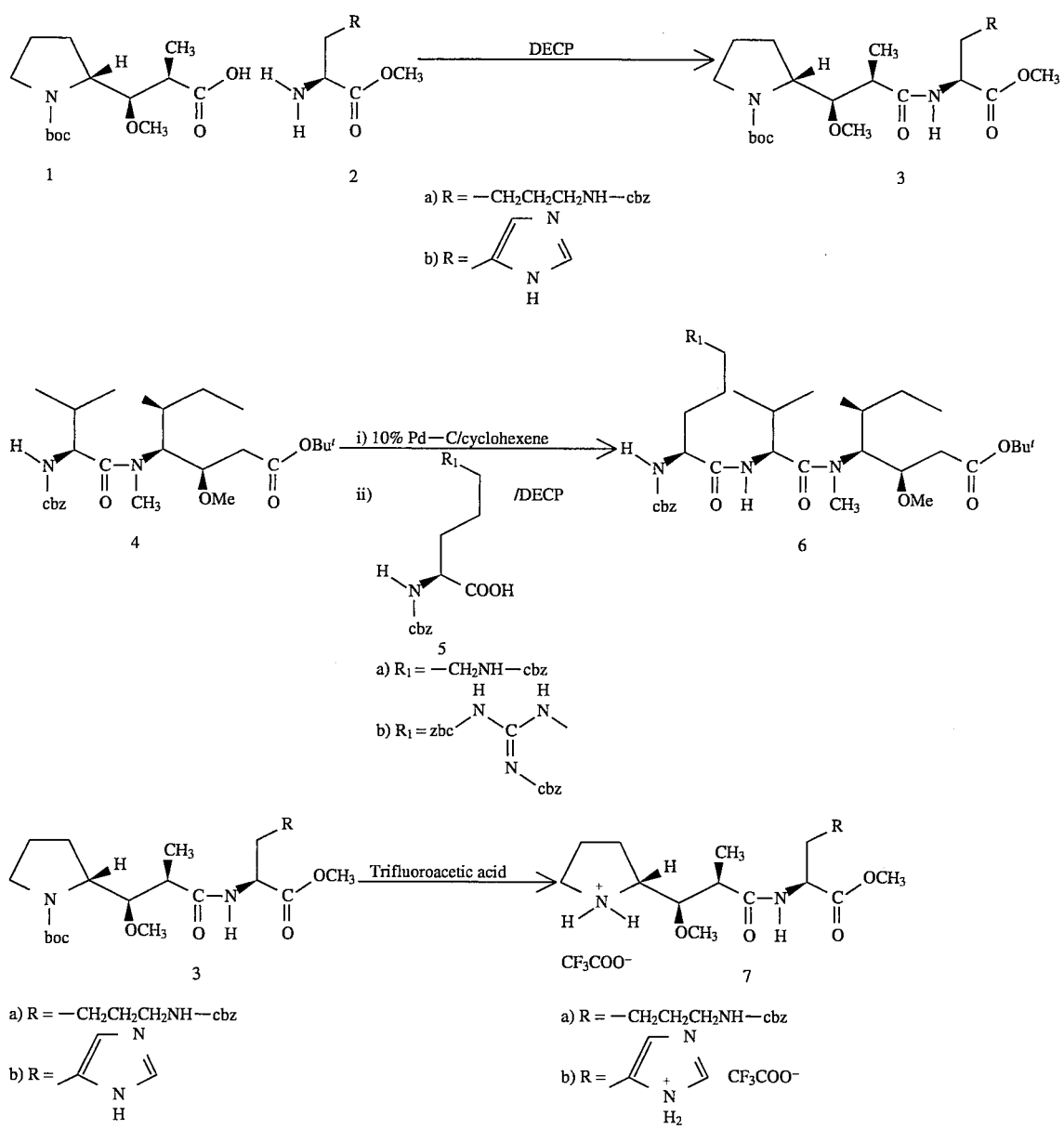

-continued

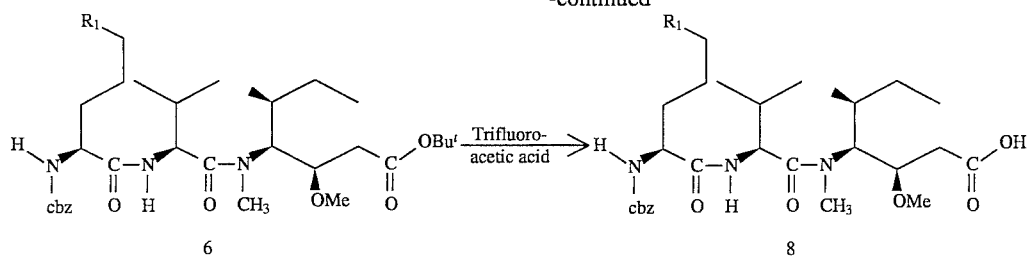

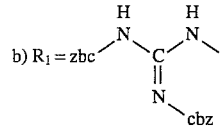

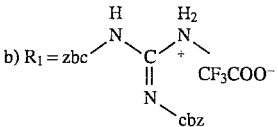

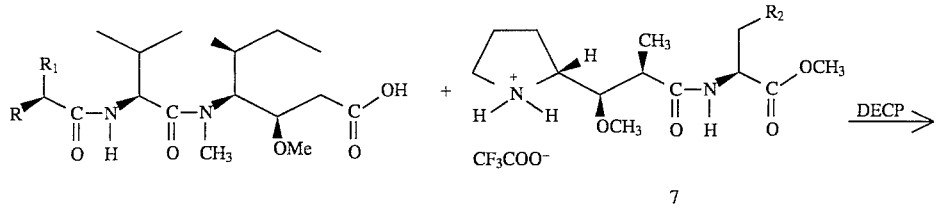

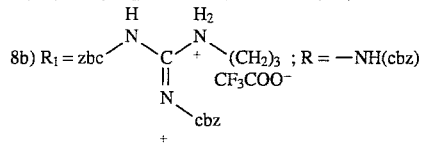

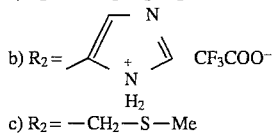

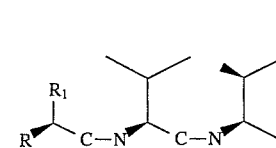

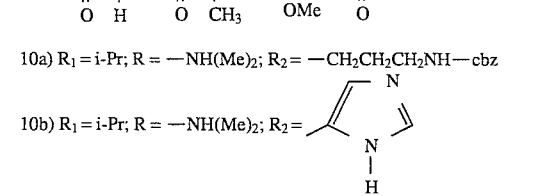

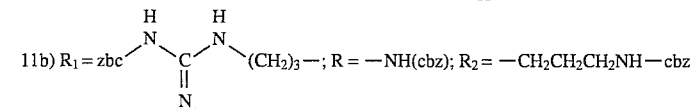

The very productive under ocean sea hare Dolabella auricularia has a number of structurally distinct peptide constituents with excellent antineoplastic activity. Presently Dolastatin 10, a linear peptide represents the most important member of the dolastatin family and is a powerful antineoplastic agent. Indeed dolastatin 10 exhibits one of the best antineoplastic activity profiles presently known against various human and animal cancer evaluation systems. The present disclosure reveals methodology that leads to several useful structural variations which substantially alter the cytotoxicity of dolastatin 10.

The new peptides disclosed here involve introduction of a peptide bond between different amino acids (2, 5) and modified amino acids (1, 4) and coupling of the resulting di- and tri- peptides to form new pentapeptide methyl esters (10, 11).

The amino acid methyl esters $N^\epsilon$ —Z—Lys—OMe(2a) and His—OMe(2b) were coupled with t—boc—dolaproine (1) in the presence of diethyl cyanophosphonate(DECP) and triethylamine leading to the formation of the protected dipeptide methyl esters (3a–b) in good yields. Similarly the N-protected amino acids 5: $N^\epsilon,N^\alpha$—di—Z—lysine (5a) and $N^\gamma,N^\gamma,N^\alpha$—tri—Z—arginine (5b) were each coupled with the dipeptide t-butyl ester 4(after deprotection of the carbobenzyloxy group by hydrogenation) in the presence of diethyl cyanophosphonate(DECP) and triethylamine leading to the formation of N-protected tripeptide t-butyl esters 6a–b in workable yields.

The protecting groups of the above mentioned dipeptide methyl esters 3a–b were removed with trifluoroacetic acid to afford the corresponding trifluoroacetate salts 7a–b. Similarly, the t-butyl protecting group in the tripeptides 6a–b was also removed with trifluoroacetic acid to yield the corresponding free acids 8a–b. Diethyl cyanophosphonate was used again with excellent results for the coupling of known tripeptide trifluoroacetate (TFA, Dov—Val—Dil—OH, 9) with each of the dipeptide salts (7a–b) to yield Dolastatin 10 structural modifications 10a–b. Similarly, the tripeptide free acids (8a–b) were coupled with the dipeptide tfa salts (7a–c) to afford the new pentapeptides (11a–c).

Accordingly, a principle objective of the present invention is to provide for the synthesis of selected derivatives of dolastatin 10 which have distinct in vitro cytostatic or neoplastic activity.

Another object of the present invention is to identify active portions of dolastatin 10 derivatives which can be attached to other molecules to provide an equally effective, but considerably less expensive tumor inhibiting agent.

These and still further objects as shall hereinafter appear are readily fulfilled by the present invention in a remarkably unexpected manner as will be readily discerned from the following detailed description of exemplary embodiments thereof.

DESCRIPTION OF THE PREFERRED EMBODIMENT

In vitro testing is an absolutely essential factor in the ongoing venture to discover new compounds for use in fighting the ravages of cancer. Without such screening, the process of obtaining new candidate drugs would be even more complex and expensive, if not impossible. To understand this process, and recognize the outstanding results demonstrated by some of the compositions disclosed herein, one must first understand the procedures, the nomenclature, and the data analysis involved. A brief description of the appropriate terminology follows:

$ED_{50}$ (P388) and $GI_{50}$ (HTCL) identify the drug dose which reduces the percent tumor/cell growth to 50%. There is no mathematical difference between $ED_{50}$ and $GI_{50}$, both of which are calculated using the same formula. The only difference is historical usage.

TGI, means "Total Growth Inhibition" and identifies the drug dose needed to yield zero percent growth, i.e. there are just as many cells at the end of the experiment as were present at the beginning. Whether just as many cells were killed as were produced (steady state), or no growth occurred (total inhibition) cannot be distinguished.

$LC_{50}$, means "Lethal Concentration 50%", and identifies the drug concentration which reduces to one-half of the cells originally present at the beginning of the experiment.

Each drug is tested at five (5) doses: 100 - 10 - 1 - 0.1 - 0.01 - µg/ml. Percent Growths are calculated for each dose. The two (or three) doses with growth values above, below, (or near to) 50% growth are used to calculate the $ED_{50}/GI_{50}$ values using a linear regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

At the start of each experiment, cells from the in vitro cell cultures are inoculated into the appropriate tubes or microtiter plates. One set of control tubes/plates is immediately counted to determine the number of cells at the start of the experiment. This is the "baseline count" or "Tzero reading". At the end of the experiment (48 hrs later), a second set of control tubes/plates is analyzed to determine the "Control Growth" value. The growth (or death) of cells relative to the initial quantity of cells is used to define the "Percent of Growth."

EXAMPLE

|  |  |
|---|---|
|  | Baseline Count 20 |
|  | Control Count 200 |
|  | (10-Fold Growth) |
| 100% Growth = Control Growth | 100% Growth = 200 |
| 50% Growth = Tzero + $\frac{\text{Control} - \text{Tzero}}{2}$ | 50% Growth = 110 |
| 0% Growth = Tzero | 0% Growth = 20 |
| −50% Growth = Tzero/2 | −50% Growth = 10 |

Now that the relevant definitions and data analysis techniques have been disclosed, this disclosure can now turn to the particular compounds disclosed herein.

The synthesis of potentially useful peptides presents one of the most essential and promising approaches to new types of anticancer and immunosuppressant drugs. The Dolastatins, an unprecedented series of linear and cyclic antineoplastic and/or cytostatic peptides isolated from Indian Ocean sea hare Dolabella auricularia represent excellent leads for synthetic modification. The very productive sea hare Dolabella auricularia has produced a number of structurally distinct peptides with excellent antineoplastic activity. Presently Dolastatin 10, a linear pentapeptide, represents the most important member and is a potentially useful antineoplastic agent. Dolastatin 10 shows one of the best antineoplastic activity profiles against various cancer screens presently known. Recently the total synthesis and absolute configuration of this structurally unique and biologically active peptide was discovered. This compound has been tested in vivo and demonstrated significant activity, as shown below.

| Experimental Anticancer Activity of Dolastatin 10 in Murine in vivo Systems, T/C (µg/kg) | |
|---|---|
| P388 Lymphocytic Leukemia | B16 Melanoma |
|  | 238 and 40% cures (11.11) |
| toxic (13.0) | 182 (6.67) |
| 155 and 17% cures (6.5) | 205 (4.0) |
| 146 and 17% cures (3.25) | 171 (3.4) |
| 137 (1.63) | 142 (1.44) |

Experimental Anticancer Activity of Dolastatin 10 in Murine in vivo Systems, T/C (μg/kg)

| | M5076 Ovary Sarcoma |
|---|---|
| L1210 Lymphocytic Leukemia | toxic (26) |
| | 166 (13) |
| 152 (13) | 142 (6.5) |
| 135 (6.5) | 151 (3.25) |
| 139 (3.25) | |
| 120 (1.63) | LOX Human Melanoma Xenograph (Nude Mouse) |
| | toxic (52) |
| | 301 and 67% cures (26) |
| | 301 and 50% cures (13) |
| | 206 and 33% cures (6.5) |
| | 170 and 17% cures (3.25) |
| | LOX in separate experiments |
| | 340 and 50% cures (43) |
| | 181 and 33% cures (26) |
| | 192 (15) |
| | 138 and 17% cures (9.0) |
| | Human Mammary Xenograph Nude Mouse |
| | Toxic (26) |
| | 137 (13) |
| | 178 (6.25) |
| | OVCAR-3 Human Ovary Xenograph Nude Mouse |
| | 300 (40) |
| | MX-1 Human Mammary Xenograft (Tumor Regression) |
| | 14 (52) |
| | 50 (26) |
| | 61 (13) |
| | 69 (6.25) |

Dolastatin 10 has also been tested against a minipanel from the NCI Primary screen. These results appear below, showing the amount of Dolastatin 10 required to attain $GI_{50}$ in μg/ml, against the cell lines set forth below.

$$\frac{OVCAR-3}{9.5 \times 10^{-7}} \text{ (A)} \quad \frac{SF\ 295}{7.6 \times 10^{-8}} \text{ (B)} \quad \frac{A498}{2.6 \times 10^{-5}} \text{ (C)}$$

$$\frac{NCI-H460}{3.4 \times 10^{-6}} \text{ (D)} \quad \frac{KM2OL2}{4.7 \times 10^{-6}} \text{ (E)} \quad \frac{SK-MEL-5}{7.4 \times 10^{-6}} \text{ (F)}$$

TABLE 1

Human Cancer-Cell line and PS-388 ($ED_{50}$) Mouse Leukemia data for the Pentapeptide Methyl Esters 10(a–b) and 11(a–c).

| | Cell type | Cell line | 10a | 10b | 11a |
|---|---|---|---|---|---|
| GI-50 (μg/ml) | Ovarian | OVCAR-3 | 0.0069 | 0.00071 | 0.12 |
| | CNS | SF-295 | >0.01 | >0.01 | 0.67 |
| | Renal | A498 | >0.01 | >0.01 | >1 |
| | Lung-NSC | NCI-H460 | >0.01 | >0.01 | 0.27 |
| | Colon | KM2OL2 | >0.01 | 0.00099 | 0.29 |
| | Melanoma | SK-MEL-5 | 0.003 | 0.0008 | 0.08 |
| TGI (μg/ml) | Ovarian | OVCAR-3 | >0.01 | >0.01 | 0.67 |
| | CNS | SF-295 | >0.01 | >0.01 | >1 |
| | Renal | A498 | >0.01 | >0.01 | >1 |
| | Lung-NSC | NCI-H460 | >0.01 | >0.01 | >1 |
| | Colon | KM2OL2 | >0.01 | >0.01 | >1 |
| | Melanoma | SK-MEL-5 | >0.01 | >0.01 | >1 |
| LC-50 (μg/ml) | Ovarian | OVCAR-3 | >0.01 | >0.01 | >1 |
| | CNS | SF-295 | >0.01 | >0.01 | >1 |
| | Renal | A498 | >0.01 | >0.01 | >1 |
| | Lung-NSC | NCI-H460 | >0.01 | >0.01 | >1 |
| | Colon | KM2OL2 | >0.01 | >0.01 | >1 |
| | Melanoma | SK-MEL-5 | >0.01 | >0.01 | >1 |
| ED-50 (μg/ml) | Mouse Leukemia | PS-388 | >0.01 | >0.01 | >1 |
| | Cell type | Cell line | 11b | 11c | |
| GI-50 (μg/ml) | Ovarian | OVCAR-3 | >1 | 0.074 | |
| | CNS | SF-295 | >1 | 0.13 | |
| | Renal | A498 | >1 | 0.6 | |
| | Lung-NSC | NCI-H460 | >1 | 0.25 | |
| | Colon | KM2OL2 | >1 | 0.28 | |
| | Melanoma | SK-MM5 | >1 | 0.38 | |
| TGI (μg/ml) | Ovarian | OVCAR-3 | >1 | 0.74 | |
| | CNS | SF-295 | >1 | >1 | |
| | Renal | A498 | >1 | >1 | |
| | Lung-NSC | NCI-H460 | >1 | 0.62 | |
| | Colon | KM20L2 | >1 | >1 | |
| | Melanoma | SK-MEL-5 | >1 | >1 | |
| LC-50 (μg/ml) | Ovarian | OVCAR-3 | >1 | >1 | |
| | CNS | SF-295 | >1 | >1 | |
| | Renal | A498 | >1 | >1 | |
| | Lung-NSC | NCI-H460 | >1 | >1 | |
| | Colon | KM20L2 | >1 | >1 | |
| | Melanoma | SK-MEL-5 | >1 | >1 | |
| ED-50 (μg/ml) | Mouse Leukemia | PS-388 | 0.513 | 0.329 | |

This synthesis begins with the selection of either of the two methyl esters, compounds 2a and compound 2b disclosed above. The initial portion of the synthesis then proceeds as follows, beginning with General Procedure A.

General Procedure A

To a solution of t—boc—dolaproine (1, 1 mM) and the amino acid methyl ester hydrochloride (2, 1.1 mM) in dry dichloromethane (10 mL), cooled to ice-bath temperature (0°–5° C.), was added triethylamine (3–4 mM) followed by diethyl cyanophosphonate (1.1 mM) and the resulting solution was stirred at the same temperature for 2 hours. The solvents were then removed under reduced pressure and the precipitated hydrochloride salt of triethylamine was filtered off. The residue was chromatographed over a silica gel column using suitable solvents to obtain the respective dipeptides.

For the methyl ester 2a, the synthesis of compound 3a proceeds as follows:

Coupling of t—boc—dolaproine (1) with $N^\epsilon$—Z—(S)—Lysine methyl ester hydrochloride (2a) following General Procedure A and chromatography of the residue over a silica gel column with acetone-hexane (2:3) as the solvent gave a gummy mass of the required dipeptide t—Boc—Dap—$N^\epsilon$—Z—Lys—OMe ester(3a, 50%); $R_f$=0.52 (2:3 acetone-hexane); $[\alpha]_D^{25}$=−23° (c 0.13, $CHCl_3$); IR(neat): 3320, 2972, 2936, 2878, 2361, 1734, 1719, 1696, 1686, 1672, 1655, 1559, 1539, 1474, 1456, 1437, 1402, 1366, 1341, 1250, 1173 and 1117 $cm^{-1}$; $^1$H NMR($CDCl_3$, 300 MHz): 7.24(m, 5H, ArH), 6.2, 6.8 (brs, NH—z), 4.97(s, 2H, $ARCH_2$), 4.88(brm, 1H, NH), 4.4(brm, 1H, CHNH), 3.75– 3.90(m, 1H, CHN), 3.60(s, 3H, COOMe), 3.4(brm, 1H, CH—OMe), 3.32(s, 3H, OMe ), 3.1 ( m, 4H, 2×$CH_2$—N ), 2.3 (m, 1H, CH—COOMe), 1.5–1.9, 1.2–1.4(m, 10H, 5×$CH_2$), 1.333, 1.328(brs, 9H, t—Bu) and 0.75(brd, 3H, Me); EIMS (m/z): 531($M^+$), 490, 463, 446, 431, 395, 379, 350, 323, 295, 259, 235, 210, 187, 170, 142, 114, 91(100%), 70 and 57.

For the other methyl ester 2b, a similar process to synthesize 3b is then followed:

Coupling of t—boc—dolaproine (1) with (S)—His—OMe (2b) following General Procedure A and chromatography of the residue over a silica gel column using methanol-chloroform(1:6) as the solvent gave a yellow solid which was recrystallized from acetone-hexane to afford pure crystals of t—Boc—Dap—His—OMe(3b, 33%); $R_f$= 0.3 (4:1 acetone-hexane); $[a]_D^{25}$=−11.3° (c 0.08, CHCl$_3$); IR(neat): 3244, 2976, 2951, 2933, 2879, 2837, 1748, 1684, 1539, 1478, 1456, 1435, 1402, 1367, 1310, 1285, 1256, 1171, 1112, 920, 864, 773 and 733 cm$^{-1}$; $^1$H NMR(CDCl$_3$, 300 MHz): 7.58(m, 1H, —N=CH—NH), 7.24(brs, Ar NH), 6.83(brs, 1H, ArH), 4.75(brs, 1H, NH), 3.4–3.9 (m, 3H, CH—N, CH—NH, CH—OMe), 3.70 (brs, 3H, COOMe), 3.41 (s, 3H, OMe), 3.05–3.3 ( m, 4H, CH$_2$—N, Ar—CH$_2$), 2.39 (m, 1H, CH—COOMe), 1.6–1.9(m, 4H, 2×CH$_2$), 1.45(brs, 9H, t-Bu) and 1.20(d, J=6.9 Hz, 3H, Me); EIMS (m/z): 438(M$^+$), 406, 365, 305, 254, 225, 196, 170, 136, 114, 82 and 57(100%).

The synthesis process then requires the synthesis of t-butyl esters 6 which is performed as shown below, following General Procedure B.

General Procedure B

A solution of Z—Val—Dil—OBu$^t$ (4, 1 mM) was dissolved in anhydrous methanol (5 mL) and cyclohexene (5 mL) was added to it in an argon atmosphere. 10% Pd—C (1g) was added and the mixture was refluxed for 6–10 minutes. The catalyst was removed by filtering through a pad of celite, the solvent removed under reduced pressure and the residue dried in high vacuum for 2 hours.

To a solution of the above free base and N-protected amino acid (5, 1 mM) in dry dichloromethane (5 mL) was added triethylamine (4 mM) followed by DECP (1.1 mM) at 0°–5 ° C. under argon atmosphere. After stirring at the same temperature for 2 hours, the solvent was removed and the residue chromatographed on a silica gel column with appropriate solvent system to give the required tripeptide t-butyl ester (6) as an oily liquid.

The process employed to synthesize compound 6a is as follows:

Coupling of the free base obtained from (4) with N,N—di—Z—Lys (5a) following the General Procedure B gave after purification on a silica gel column with 3:2 hexane-acetone as the eluent a clear oil (6a, 68%); $R_f$=0.26(1:3 Acetone-Hexane); $[\alpha]_D^{25}$=−22.5° (c 5.2, MeOH); IR(neat): 3310, 2962, 2935, 2867, 1718, 1635, 1523, 1456, 1415, 1392, 1369, 1342, 1248, 1153, 1097, 1028, 738, 698 and 667 cm$^{-1}$; $^1$H NMR(CDCl$_3$, 300 MHz): 7.31(m, 10H, ArH), 6.62(brd, J=7.9 Hz, 1H, NH), 5.51 (brd, J=7.1 Hz, 1H, NH), 5.07(m, 4H, 2x Ar—CH$_2$), 4.70(m, 2H, Lys C$^\alpha$—H and Val C$^\alpha$—H) 4.24(m, 1H, NH), 3.85(brm, 1H, CH—N—Me), 3.30(s, 3H, OMe), 3.14(m, 3H, CH$_2$—NH—z, CH—OMe), 2.94(s, 3H, N—Me), 2.35(m, 2H, CH$_2$—COOBu$^t$), 2.0(m, 1H, CH), 1.25–1.80(m, 9H, 4x CH$_2$, CH), 1.60, 1.44(s, 9H, t-Bu) and 0.70–1.0(m, 12H, 4x CH$_3$); EIMS (m/z): 755(M$^+$), 595, 559, 496, 451, 388, 344, 316, 263, 218, 174, 155, 127, 108 and 107(100%).

Similarly, compound 6b is obtained as follows:

Coupling of the free base obtained from (4) with N,N, N—tri—Z—(L)—Arg (5b) following the General Procedure B gave after purification on a silica gel column with 3:2 Hexane-Acetone as the eluent a colorless solid (6b, 53%); m.p.=69°–71° C.; $R_f$=0.34(1:3 Acetone-Hexane); $[\alpha]_D^{25}$=−22.7° (c 3, MeOH); IR(neat): 3387, 3293, 3065, 3034, 2967, 2934, 2878, 1719, 1645, 1636, 1616, 1506, 1456, 1412, 1379, 1256, 1179, 1154, 1099, 1011, 777, 743, 698, 619, 586 cm$^{-1}$; $^1$H NMR(CDCl$_3$, 300 MHz): 9.43(brs, 1H, NH), 9.23(brs, 1H, NH),7.21–7.38(m, 15H, 3x C$_6$H$_5$, NH), 6.77(d, J=8.8 Hz, 1H, NH), 5.93 (d, J=8.3 HZ, 1H, NH) , 4.94–5.19 (m, 6H, 3x CH$_2$—Ar) , 4.65– 4.70 (m, 2H, Arg C$^\alpha$—H, Val C$^\alpha$—H) , 4.20–4.25 (m, 1H, Dil CH—N) , 3.82–3.90(m, 3H, N—CH$_2$, CH—OCH$_3$), 3.31(s, 3H, OCH3), 2.89(s, 3H, N—CH$_3$), 2.22–2.43 (m, 2H, CH$_2$—CO), 1.89–1.96 (m, 1H, Dil CH), 1.60 (m, 7H, 3x CH$_2$, Val CH), 1.42(s, 9H, t-Bu) and 0.73–0.90(m 12H, 4x CH$_3$); EIMS (m/z): 740(M$^+$−176), 606, 581, 473, 454, 432, 410, 346, 329, 297, 238, 225, 204, 186, 162, 146, 128 and 108(100%).

The dipeptide trifluoroacetate salts (7a–b) were obtained using General Procedure C, as shown below:

General Procedure C

To a solution of t—boc—dipeptide—OMe (3a–b, 0.1 mM) in dichloromethane (2 mL) cooled to ice-bath temperature was added trifluoroacetic acid (2 mL) under argon atmosphere and the solution was stirred at the same temperature for 1 hour. The solvents were then removed under reduced pressure, the residue was dissolved in toluene and solvent again removed under reduced pressure. The residue was dried in vacuo to obtain a light yellow sticky mass of the respective dipeptide trifluoroacetate salts (7a–b).

The tripeptide trifluoroacetate salts (8a–b) were obtained using General Procedure D as shown below:

General Procedure D

To a solution of tripeptide t-butyl ester (6a–b, 0.1 mM) in dichloromethane (2 mL) cooled to ice-bath temperature was added trifluoroacetic acid (2 mL) under argon atmosphere and the solution was stirred at the same temperature for 1 hour. The solvents were then removed under reduced pressure, the residue was dissolved in toluene and solvent again removed under reduced pressure. The residue was dried in vacuo to obtain a light yellow sticky mass of the respective dipeptide trifluoroacetate salts (8a–b).

The desired pentapeptides (10, 11) were then obtained using General Procedure E, as shown below:

General Procedure E

To a solution of dipeptide tfa salt (7, 0.1 mM) and the tripeptide tfa salt (9, 8, 0.1 mM) in dry dichloromethane (2 mL), cooled to ice-bath temperature (0°–5° C.) was added triethylamine (4 mM) followed by diethyl cyanophosphonate (1.1 mM). The solution was then stirred at the same temperature for 1–2 hours. The solvent was then removed under reduced pressure and the residue chromatographed on a silica gel column using suitable solvents to obtain the respective pentapeptides (10, 11).

The precise methodology of the final synthesis is set forth below, under the name of each compound:

Dov—Val—Dil—Dap—N$^\epsilon$Z—Lys—OMe(10a):

Coupling of the dipeptide tfa salt 7a with the tripeptide tfa salt (9) following the General Procedure E gave, following purification on a silica gel column with acetone-hexane (3:1) as the eluent, the required pentapeptide was obtained as a colorless solid (10a, 26%); m.p. 98°–99° C.; $R_f$ 0.41 (acetone-hexane 4:1); [8,1 a]$_D^{25}$ −36.3° (C 0.08, CHCl$_3$); IR(thin film): 3300, 2963, 2934, 2876, 2830, 2787, 1748, 1622, 1576, 1539, 1524, 1507, 1489, 1456, 1418, 1385, 1371, 1302, 1267, 1200, 1175, 1130 and 1098 cm$^{-1}$.

Dov—Val—Dil—Dap—His—OMe(10b):

Coupling of the dipeptide tfa salt 7b with the tripeptide tfa salt (9) following the General Procedure E gave after purification on a silica gel column with methanol-chloroform (1:6) as the eluent the required pentapeptide as a colorless solid (10b, 68%); m.p. 96°– 98° C.; $R_f$ 0.49 (methanol-chloroform 1:6); $[\alpha]_D^{25}$ −33.8° (c 0.08, CHCl$_3$); IR(thin film): 3298, 3055, 2963, 2934, 2876, 2830, 2787, 1748, 1624, 1576, 1559, 1539, 1522, 1507, 1489, 1456, 1439, 1418, 1385, 1341, 1265, 1200, 1181 and 1098 cm$^{-1}$; EIMS (m/z): 749(M$^+$), 706, 649, 531, 481, 452, 409, 371, 345, 315, 285, 268, 227, 206, 191, 170, 165, 154, 128 and 101(100%).

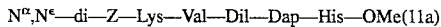
N$^\alpha$,N$^\epsilon$—di—Z—Lys—Val—Dil—Dap—His—OMe(11a)

Coupling of the dipeptide tfa salt 7b with the tripeptide tfa salt 8a following the General Procedure E and purification using chromatography on a silica gel column with chloroform-methanol (7:1) as eluent gave the required pentapeptide as a colorless solid (11a, 28%); m.p. 88°–90° C.; R$_f$ 0.58 (chloroform-methanol 6:1); $[\alpha]_D^{25}$ −33.3° (C 0.12, CHCl$_3$); IR(thin film): 3310, 3298, 2963, 2934, 2880, 2361, 2338, 1732, 1717, 1699, 1684, 1653, 1636, 1576, 1559, 1541, 1522, 1506, 1497, 1456, 1437, 1420, 1387, 1341, 1248, 1181, 1161, 1096, 1045, 1028, 752, 698, 667 and 619 cm$^{-1}$.

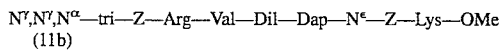
N$^\gamma$,N$^{\gamma'}$,N$^\alpha$—tri—Z—Arg—Val—Dil—Dap—N$^\epsilon$—Z—Lys—OMe (11b)

Coupling dipeptide tfa salt 7a with tripeptide tfa salt 8b following General Procedure E and purification by column chromatography on silica gel with acetone-hexane (2:1) as the eluent furnished the required pentapeptide as a colorless solid (11b, 73%); m.p. 64°–66° C.; R$_f$ 0.5 (acetone-hexane 1:1); $[\alpha]_D^{25}$ −20.6° (c 0.12, CHCl$_3$); IR(thin film): 3384, 3312, 3300, 2959, 2934, 2878, 1717, 1645, 1636, 1616, 1576, 1559, 1539, 1520, 1508, 1456, 1439, 1417, 1379, 1339, 1254, 1098, 1028, 739 and 698 cm$^{-1}$.

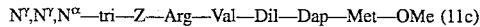
N$^\gamma$,N$^{\gamma'}$,N$^\alpha$—tri—Z—Arg—Val—Dil—Dap—Met—OMe (11c)

Coupling dipeptide tfa salt 7c with the tripeptide tfa salt 8b following General Procedure E and purification by column chromatography on silica gel with acetone-hexane (3:2) as the eluent gave the required pentapeptide as a colorless solid (11c, 77%); R$_f$ 0.62 (3:2 acetone-hexane); $[\alpha]_D^{25}$ −20° (c 0.12, CHCl$_3$); IR(neat): 3389, 3379, 3306, 3295, 2965, 2934, 2878, 1721, 1640, 1613, 1512, 1452, 1416, 1379, 1343, 1254, 1098, 1028, 980, 808, 777, 741 and 698 cm$^{-1}$.

To further aid in the understanding of the present invention, and not by way of limitation the following examples are presented.

EXAMPLE I-a

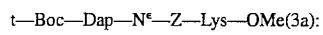
t—Boc—Dap—N$^\epsilon$—Z—Lys—OMe(3a):

Coupling of t—boc—dolaproine (1) with N$^\epsilon$—Z—(S)—Lysine methyl ester hydrochloride (2a) following General Procedure A and chromatography of the residue over a silica gel column with acetone-hexane (2:3) as the solvent gave a gummy mass of the required dipeptide t—Boc—Dap—Ne—Z—LYs OMe ester(3a, 50%); R$_f$=0.52 (2:3 acetone-hexane); $[\alpha]_D^{25}$= −23° (c 0.13, CHCl$_3$); IR(neat): 3320, 2972, 293, 2878, 2361, 1734, 1719, 1696, 1686, 1672, 1655, 1559, 1539, 1474, 1456, 1437, 1402, 1366, 1341, 1250, 1173 and 1117 cm$^{-1}$; $^1$H NMR(CDCl$_3$, 300 MHz): 7.24 (m, 5H, ArH), 6.2, 6.8 (brs, NH—z), 4.97(s, 2H, ARCH$_2$), 4.88(brm, 1H, NH), 4.4(brm, 1H, CHNH), 3.75– 3.90(m, 1H, CHN), 3.60(s, 3H, COOMe), 3.4(brm, 1H, CH—OMe), 3.32(s, 3H, OMe), 3.1(m, 4H, 2×CH$_2$—N), 2.3(m, 1H, CH—COOMe), 1.5–1.9, 1.2–1.4(m, 10H, 5×CH$_2$), 1.33, 1.32(brs, 9H, t—Bu) and 0.75(brd, 3H, Me); EIMS (m/z): 531(M$^+$), 490, 463, 446, 431, 395, 379, 350, 323, 295, 259, 235, 210, 187, 170, 142, 114, 91(100%), 70 and 57.

EXAMPLE I-b

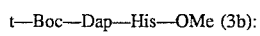
t—Boc—Dap—His—OMe (3b):

Coupling of t—boc—dolaproine (1) with (S)—His—OMe following General Procedure A and chromatography of the residue over a silica gel column using methanol-chloroform (1:6) as the solvent gave a yellow solid which was recrystallized from acetone-hexane to afford pure crystals of t—Boc—Dap—His—OMe(3b, 33%); R$_f$= 0.3 ( 4: 1 acetone-hexane ); $[\alpha]_D^{25}$=−11.3° (c 0.08, CHCl$_3$); IR(neat): 3244, 2976, 2951, 2933, 2879, 2837, 1748, 1684, 1539, 1478, 1456, 1435, 1402, 1367, 1310, 1285, 1256, 1171, 1112, 920, 864, 773 and 733 cm$^{-1}$; $^1$H NMR(CDCl$_3$, 300 MHz): 7.58(m, 1H, −N=CH—NH), 7.24(brs, Ar NH), 6.83(brs, 1H, ArH), 4.75(brs, 1H, NH), 3.4–3.9 (m, 3H, CH—N, CH—NH, CH—OMe), 3.70(brs, 3H, COOMe), 3.41(s, 3H, OMe), 3.05–3.3(m, 4H, CH$_2$—N, Ar—CH$_2$), 2.39 (m, 1H, CH—COOMe), 1.6–1.9 (m, 4H, 2x CH$_2$), 1.45(brs, 9H, t-Bu) and 1.20(d, J=6.9 Hz, 3H, Me); EIMS (m/z): 438 (M$^+$) , 406, 365, 305, 254, 225, 196, 170, 136, 114, 82 and 57(100%).

EXAMPLE II-a

N$^\epsilon$—di—Z—Lys—Val—Dil—OBu$^t$(6a):

Coupling of the free. base obtained from (4) with N,N—di—Z—Lys (5a) following the General Procedure B gave after purification on a silica gel column with 3:2 hexane-acetone as the eluent a clear oil (6a, 68%); R$_f$=0.26(1:3 Acetone-Hexane); $[\alpha]_D^{25}$ =−22.5° (c 5.2, MeOH); IR(neat): 3310, 2962, 2935, 2867, 1718, 1635, 1523, 1456, 1415, 1392, 1369, 1342, 1248, 1153, 1097, 1028, 738, 698 and 667 cm$^{-1}$; $^1$H NMR(CDCl$_3$, 300 MHz): 7.31(m, 10H, ArH), 6.62(brd, J=7.9 Hz, 1H, NH), 5.51 (brd, J=7.1 Hz, 1H, NH), 5.07 (m, 4H, 2x Ar—CH$_2$), 4.70 (m, 2H, Lys C$^\alpha$—H and Val C$^\alpha$H) 4.24 (m, 1H, NH), 3.85(brm, 1H, CH—N—Me), 3.30(s, 3H, OMe), 3.14(m, 3H, CH$_2$—NH—z, CH—OMe), 2.94(s, 3H, N—Me), 2.35 (m, 2H, CH$_2$—COOBu$^t$), 2.0(m, 1H, CH), 1.25–1.80(m, 9H, 4x CH$_2$, CH), 1.60, 1.44(s, 9H, t-Bu) and 0.70–1.0(m, 12H, 4x CH$_3$); EIMS (m/z): 755(M$^+$), 595, 559, 496, 451, 388, 344, 316, 263, 218, 174, 155, 127, 108 and 107(100%).

EXAMPLE II-b

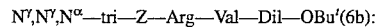
N$^\gamma$,N$^{\gamma'}$,N$^\alpha$—tri—Z—Arg—Val—Dil—OBu$^t$(6b):

Coupling of the free base obtained from (4) with N,N,N—tri—Z—(L) —Arg (5b) following the General Procedure B gave after purification on a silica gel column with 3:2 Hexane-Acetone as the eluent a colorless solid (6b, 53%); m.p.=69°–71° C.; R$_f$=0.34(1:3 Acetone-Hexane); $[\alpha]_D^{25}$=−22.7° (c 3, MeOH); IR(neat): 3387, 3293, 3065, 3034, 2967, 2934, 2878, 1719, 1645, 1636, 1616, 1506, 1456, 1412, 1379, 1256, 1179, 1154, 1099, 1011, 777, 743, 698, 619, 586 cm$^{-1}$; $^1$H NMR(CDCl$_3$, 300 MHz): 9.43 (brs, 1H, NH), 9.23 (brs, 1H, NH) ,7.21–7.38(m, 15H, 3x C$_6$H$_5$, NH) , 6.77(d, J=8.8 Hz, 1H, NH) , 5.93 (d, J=8.3 Hz, 1H, NH), 4.94–5.19 (m, 6H, 3x CH$_2$—Ar), 4.65– 4.70 (m, 2H, Arg C$^\alpha$—H, Val C$^\alpha$—H) 4.20–4.25(m, 1H, Dil CH—N) , 3.82– 3.90 ( m, 3H, N—CH$_2$, CH—OCH$_3$), 3.31 (s, 3 H, OCH$_3$), 2.89(s, 3H, N—CH$_3$), 2.22–2.43(m, 2H, CH$_2$—CO), 1.89–1.96 (m, 1H, Dil CH), 1.60(m, 7H, 3x CH$_2$, Val CH), 1.42(s, 9H, t-Bu) and 0.73–0.90(m 12H, 4x CH$_3$); EIMS (m/z): 740(M$^+$−176), 606, 581, 473, 454, 432, 410, 346, 329, 297, 238, 225, 204, 186, 162, 146, 128 and 108(100%).

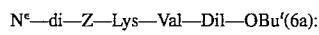

EXAMPLE III

Synthesis of the dipeptide trifluoroacetate salts(7a–b)

To a solution of t—boc—dipeptide—OMe (3a–b, 0.1 mM) in dichloromethane (2 mL) cooled to ice-bath temperature was added trifluoroacetic acid (2 mL) under argon atmosphere and the solution was stirred at the same temperature for 1 hour. The solvents were then removed under reduced pressure, the residue was dissolved in toluene and solvent again removed under reduced pressure. The residue was dried in vacuo to obtain a light yellow sticky mass of the respective dipeptide trifluoroacetate salts (7a–b).

EXAMPLE IV

Synthesis of the tripeptide trifluoroacetate salts (8a–b)

To a solution of tripeptide t-butyl ester (6a–b, 0.1 mM) in dichloromethane (2 mL) cooled to ice-bath temperature was added trifluoroacetic acid (2 mL) under argon atmosphere and the solution was stirred at the same temperature for 1 hour. The solvents were then removed under reduced pressure, the residue was dissolved in toluene and solvent again removed under reduced pressure. The residue was dried in Vacuo to obtain a light yellow sticky mass of the respective dipeptide trifluoroacetate salts (8a–b).

EXAMPLE V

Synthesis of the human cancer active pentapeptides (10a–b, 11a–c)

EXAMPLE V-a

Dov—Val—Dil—Dap—N$^\epsilon$—Z—Lys—OMe (10a):

Coupling of the dipeptide tfa salt 7a with the tripeptide tfa salt 9 following the General Procedure E gave, following purification on a silica gel column with acetone-hexane (3:1) as the eluent, the required pentapeptide as a colorless solid (10a, 26%); m.p. 98°–99° C; $R_f$ 0.41 (acetone-hexane 4:1); $[\alpha]_D^{25}$ –36.3° (c 0.08, CHCl$_3$); IR(thin film): 3300, 2963, 2934, 2876, 2830, 2787, 1748, 1622, 1576, 1539, 1524, 1507, 1489, 1456, 1418, 1385, 1371, 1302, 1267, 1200, 1175, 1130 and 1098 cm$^{-1}$.

EXAMPLE V-b

Dov—Val—Dil—Dap—His—OMe (10b):

Coupling of the dipeptide tfa salt 7b with the tripeptide tfa salt 9 following the General Procedure E gave after purification on a silica gel column with methanol-chloroform (1:6) as the eluent the required pentapeptide as a colorless solid (10b, 68%); m.p. 96°– 98° C.; $R_f$ 0.49 (methanol-chloroform 1:6); $[\alpha]_D^{25}$ –33.8° (c 0.08, CHCl$_3$); IR(thin film): 3298, 3055, 2963, 2934, 2876, 2830, 2787, 1748, 1624, 1576, 1559, 1539, 1522, 1507, 1489, 1456, 1439, 1418, 1385, 1341, 1265, 1200, 1181 and 1098 cm$^{-1}$; EIMS (m/z): 749(M$^+$), 706, 649, 531, 481, 452, 409, 371, 345, 315, 285, 268, 227, 206, 191, 170, 165, 154, 128 and 101(100%).

EXAMPLE VI

Synthesis of the human cancer active pentapeptides (11a–c)

EXAMPLE VI-a

N$^\alpha$,N$^\epsilon$—di—Z—Lys—Val—Dil—Dap—His—OMe(11a)

Coupling of the dipeptide tfa salt 7b with the tripeptide tfa salt 8a following the General Procedure E and purification using chromatography on a silica gel column with chloroform-methanol (7:1) as eluent gave the required pentapeptide as a colorless solid (11a, 28%); m.p. 88°–90° C.; $R_f$ 0.58 (chloroform-methanol 6:1); $[\alpha]_D^{25}$ –33.3° (c 0.12, CHCl$_3$); IR(thin film): 3310, 3298, 2963, 2934, 2880, 2361, 2338, 1732, 1717, 1699, 1684, 1653, 1636, 1576, 1559, 1541, 1522, 1506, 1497, 1456, 1437, 1420, 1387, 1341, 1248, 1181, 1161, 1096, 1045, 1028, 752, 698, 667 and 619 cm$^{-1}$.

EXAMPLE VI-b

N$^\gamma$,N$^\gamma$,N$^\alpha$—tri—Z—Arg—Val—Dil—Dap—N$^\epsilon$—Z—Lys—OMe (11b)

Coupling dipeptide tfa salt 7a with tripeptide tfa salt 8b following General Procedure E and purification by column chromatography on silica gel with acetone-hexane (2:1) as the eluent furnished the required pentapeptide as a colorless solid (11b, 73%); m.p. 64°–66° C.; $R_f$ 0.5 (acetone-hexane 1:1); $[\alpha]_D^{25}$ –20.6° (C 0.12, CHCl$_3$); IR(thin film): 3384, 3312, 3300, 2959, 2934, 2878, 1717, 1645, 1636, 1616, 1576, 1559, 1539, 1520, 1508, 1456, 1439, 1417, 1379, 1339, 1254, 1098, 1028, 739 and 698 cm$^{-1}$.

EXAMPLE VI-c

N$^\gamma$,N$^\gamma$,N$^\alpha$—tri—Z—Arg—Val—Dil—Dap—Met—OMe (11c)

Coupling dipeptide tfa salt 7c with the tripeptide tfa salt 8b following General Procedure E and purification by column chromatography on silica gel with acetone-hexane (3:2) as the eluent gave the required pentapeptide as a colorless solid (11c, 77%); $R_f$ 0.62 (3:2 acetone-hexane); $[\alpha]_D^{25}$ –20° (c 0.12, CHCl$_3$); IR(neat): 3389, 3379, 3306, 3295, 2965, 2934, 2878, 1721, 1640, 1613, 1512, 1452, 1416, 1379, 1343, 1254, 1098, 1028, 980, 808, 777, 741 and 698 cm$^{-1}$.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. A composition of matter having the general structure shown below wherein:

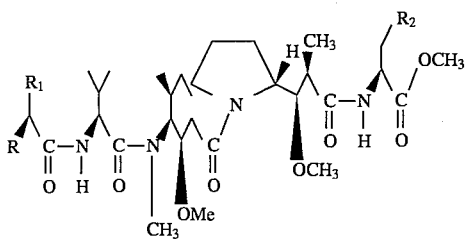

10a) R$_1$ = i-Pr; R = —NH(Me)$_2$; R$_2$ = —CH$_2$CH$_2$CH$_2$NH-cbz

10b)  $R_1$ = i-Pr; $R$ = —NH(Me)$_2$; $R_2$ = 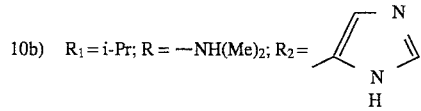

11a)  $R_1$ = —(CH$_2$)$_4$NH-cbz; $R$ = —NH(cbz);

$R_2$ = 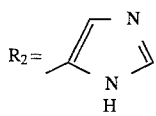

11b)  $R_1$ = zbc 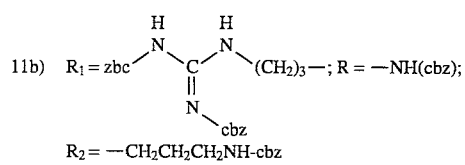 (CH$_2$)$_3$—; $R$ = —NH(cbz);

$R_2$ = —CH$_2$CH$_2$CH$_2$NH-cbz

11c)  $R_1$ = zbc 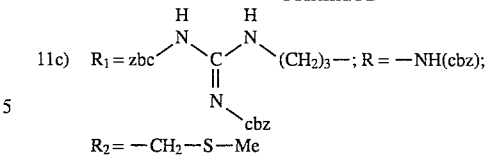 (CH$_2$)$_3$—; $R$ = —NH(cbz);

$R_2$ = —CH$_2$—S—Me

R is selected from the group consisting of the substituents shown above, $R_1$ is selected from the group consisting of the substituents shown above, and R2 is selected from the group consisting of the substituents shown above.

2. A composition of matter according to claim 1 designated herein as compound "10a".

3. A composition of matter according to claim 1 designated herein as compound "10b".

4. A composition of matter according to claim 1 designated herein as compound "11a."

5. A composition of matter according to claim 1 designated herein as compound "11b."

6. A composition of matter according to claim 1 designated herein as compound "11c."

* * * * *